United States Patent [19]
Harada

[11] 3,934,100
[45] Jan. 20, 1976

[54] ACOUSTIC COUPLER FOR USE WITH AUDITORY EQUIPMENT

[75] Inventor: Mas Harada, Minneapolis, Minn.

[73] Assignee: Seeburg Corporation, Chicago, Ill.

[22] Filed: Apr. 22, 1974

[21] Appl. No.: 462,814

[52] U.S. Cl............................................ 179/182 R
[51] Int. Cl.²........................................... H04R 1/10
[58] Field of Search...... 179/182 R, 107 E, 107 FD, 179/107 S, 1 P, 1 S; 181/33 R

[56] References Cited
UNITED STATES PATENTS

| | | | |
|---|---|---|---|
| 3,637,040 | 1/1972 | Gorman............................ | 181/33 R |
| 3,702,123 | 11/1972 | Macken et al. .............. | 179/107 E X |

FOREIGN PATENTS OR APPLICATIONS

| | | | |
|---|---|---|---|
| 1,142,120 | 9/1957 | France............................ | 179/107 E |

*Primary Examiner*—Thomas W. Brown
*Attorney, Agent, or Firm*—Schroeder Siegfried Ryan & Vidas

[57] ABSTRACT

The disclosure is directed to an elongated and tapered, bulb-like hollow housing which is constructed and arranged to fit in the outer ear of the wearer having a plurality of openings formed therein circumferentially disposed to define rib portions which are substantially parallel to the longitudinal axis of the housing. The tapered end has a small opening formed therein which by comparison is substantially smaller in diameter than that of the bulb-like hollow housing. A flexible conduit which has one end adapted to fit a sound transmitting device, such as a hearing aid or other acoustical device has the other end extending through the hollow housing into the small opening in an acoustic coupling relationship. An end cap in the form of a disc may be secured in the larger open end of the tapered cylindrical housing to receive the flexible conduit and may also be formed with a number of apertures therein. Two discs may also be used to control the size of the openings by using a side-by-side arrangement.

5 Claims, 3 Drawing Figures

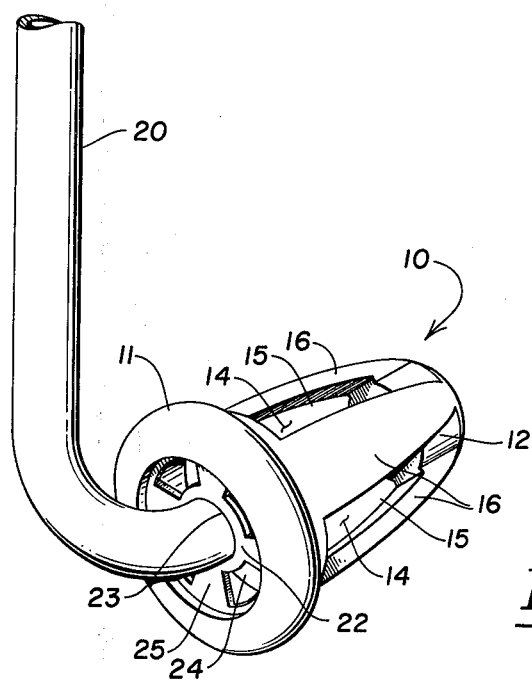
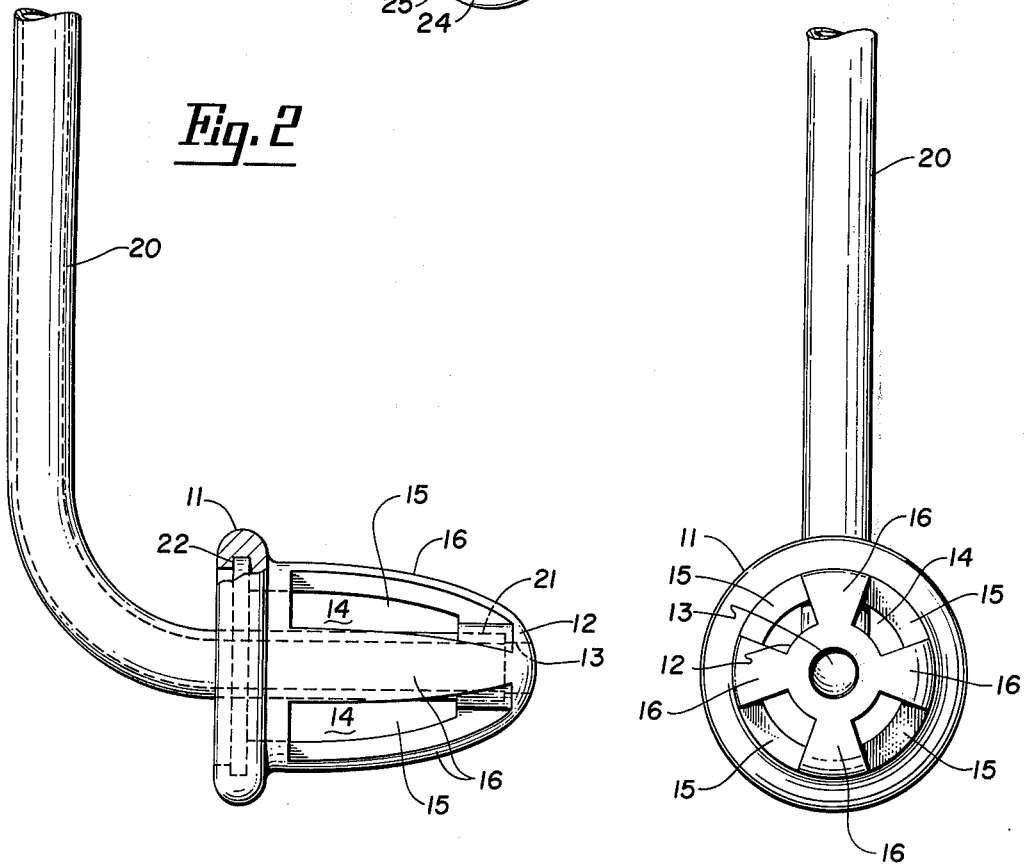

ACOUSTIC COUPLER FOR USE WITH AUDITORY EQUIPMENT

This invention relates to the field of acoustic devices and more particularly to the field of acoustic coupling seals for use with a sound transmitting tube which is directed into the outer ear.

Certain forms of hearing aids, dictating machines, tape players, and telephones presently being used today no longer use the ear mold or ear tip which forms a tight acoustic seal with the ear canal thus excluding all outside sounds. This has generally been the case because of the physical arrangement of the components within the hearing aid producing feedback which is highly undesirable for the wearer. However, with certain types of hearing losses, the acoustic tube may be introduced into the ear canal with no mold or other tip closing the space between the ear canal and the outer configuration of the tube. With this type of hearing loss, the hearing aid amplifies the higher pitched sounds which are then carried to the ear drum through the tube and the lower ranges are permitted to reach the ear drum directly. However, it is also undesirable to have the acoustic tube merely dangling in the outer ear or movable so as to contact the outer ear in a loose arrangement.

Certain present day dictating equipment, radios, and telephones make it desirable to be able to receive normal sounds as well as those being amplified at the same time.

The present invention is directed to an ear tip which also forms an acoustic connection or coupling to carry out the provisions of permitting the higher pitched sounds to be amplified through a hearing aid or other amplifier and permitting the lower pitched and normal sounds to be received directly into the ear. The ear tip is formed of a soft plastic material and openings are formed around the outer portion of the tube which extends into the tip member much like the openings between the spokes of a wheel. It has also been found that it is desirable in some cases to be able to regulate the amplitude and control the frequency of the sound received in this manner and a disc is also provided which has apertures formed therein which may be used for increasing or reducing the amplitude of the lower pitched and other normal sounds received directly.

It is therefore a general object of the present invention to provide an improvement in ear tips used with hearing aids and other electro-acoustic devices.

It is a more specific object of this invention to provide an acoustic coupling for use with a sound carrying tube which admits lower range and normal sounds to the ear directly.

These and other objects and advantages of the invention will more fully appear from the following description, made in connection with the accompanying drawings, wherein like reference characters refer to the same or similar parts throughout the several views, and in which:

FIG. 1 is a perspective view of the acoustic seal used with a sound tube;

FIG. 2 is an elevational side view of the acoustic seal used with a sound tube; and FIG. 3 is an elevational end view of the acoustic seal used with a sound tube as fitted in the ear.

As shown in the Figures, an acoustic coupler 10 is shown which has an elongated and tapered bulb-like hollow housing 11 which is of a proper dimension to be fitted in the outer ear of the wearer. It has been found that the outer diameter is generally between the dimensions of 0.265 inches and 0.335 inches depending upon the size of the ear canal of the wearer. The general length of housing 11 is approximately one-half to three-fourths of an inch with the thickness of the outer shell being approximately 1/32 to 3/32 of an inch. The tapered housing 11 has an end 2 and an inner opening 14 which communicates with an opening 13 formed in 12. Portions of the outer housng 11 are exposed providing a plurality of openings 15 which, because of their symmetrical relationship, form a plurality of ribs 16 which are formed substantially parallel to the longitudinal axis of member 11. The ribs 16 may also be formed like screw threads if desirable, as long as adequate openings are formed between them.

A flexible conduit 20 has one end adapted to be fitted to a sound transmitting device such as a hearing aid or other devices described earlier and has a second end 21 which extends through opening 14 in the hollow housing into opening 13.

To provide additional support, but more particularly to provide a means for reducing the amplitude of outside sounds, a circular disc 22 may be used, and when used, is secured in the larger end of housing 11 through the use of an annular groove which releasably secures disc 22 in a radial manner at a normal open position of housing 11. Disc 22 has a central opening 23 for receiving flexible conduit 20 and also includes a plurality of apertures 24 which are formed by a plurality of intermediate members 25 like spokes or round openings, etc. in a wheel. The openings in disc 22 may be circular in nature and disc 22 may also be made in two cooperating parts to adjust the size of apertures 24. Generally speaking, the total area of the plurality of apertures 24 are substantially larger than central opening 23. Using the acoustic coupler disclosed herein, a wearer is able to take advantage of the amplified higher pitched sounds emanating from a hearing aid or other device and the lower pitched and normal sounds which may be received directly in the ear canal.

It will, of course, be understood that various changes may be made in the form, details, arrangement and proportions of the parts without departing from the scope of the invention which consists of the matter shown and described herein and set forth in the appended claims.

What is claimed is:

1. An acoustic coupler for use with a sound carrying tube directed into the outer ear, said coupler comprising:
   a. an elongated and tapered bulb-like hollow housing constructed and arranged to fit in the outer ear of a wearer and having a plurality of openings formed therein circumferentially disposed to define rib portions in said hollow housing;
   b. said tapered hollow housing having a small end portion with a first opening formed therein substantially smaller in diameter than that of said bulb-like hollow housing;
   c. and a flexible conduit having a first end adapted to be fitted to a sound transmitting device and having a second end extending through said hollow housing into acoustic sealing relationship with said first opening in said end portion.

2. The structure set forth in claim 1 including:

d. an end cap releasably secured in the largest end of said tapered cylindrical hollow housing and radially disposed therein, said end cap having a central opening for receiving said flexible conduit and a plurality of apertures radially disposed around said central opening.

3. The structure set forth in claim 1 wherein said rib portions of said elongated and tapered bulb-like hollow housing are formed substantially parallel to the longitudinal axis thereof.

4. The structure set forth in claim 2 wherein said plurality of apertures in said end cap have a total area substantially larger than said central opening.

5. The structure set forth in claim 2 wherein said end cap is formed of a pair of cooperating discs, each containing a plurality of apertures in which said discs may be rotated to vary said apertures to a predetermined effective area.

* * * * *